(12) United States Patent
Gu et al.

(10) Patent No.: US 7,538,119 B2
(45) Date of Patent: May 26, 2009

(54) 41-METHOXY ISOTOPE LABELED RAPAMYCIN 42-ESTER

(75) Inventors: Jianxin Gu, River Edge, NJ (US); Mark Ruppen, Garnerville, NY (US)

(73) Assignee: Wyeth, Madison, NJ (US)

( * ) Notice: Subject to any disclaimer, the term of this patent is extended or adjusted under 35 U.S.C. 154(b) by 331 days.

(21) Appl. No.: 11/592,518

(22) Filed: Nov. 3, 2006

(65) Prior Publication Data

US 2007/0105888 A1    May 10, 2007

Related U.S. Application Data

(60) Provisional application No. 60/733,563, filed on Nov. 4, 2005.

(51) Int. Cl.
*C07D 498/18* (2006.01)
*A61K 31/395* (2006.01)
*A61P 35/00* (2006.01)

(52) U.S. Cl. ..................... 514/291; 540/456

(58) Field of Classification Search ........... 540/456; 514/291
See application file for complete search history.

(56) References Cited

U.S. PATENT DOCUMENTS

| 5,362,718 | A  | 11/1994 | Skotnicki et al. |
|-----------|----|---------|------------------|
| 6,277,983 | B1 | 8/2001  | Shaw et al.      |
| 2003/0130206 | A1 | 7/2003 | Koziak et al. |
| 2004/0077677 | A1 | 4/2004 | Ashraf et al. |
| 2004/0167152 | A1 | 8/2004 | Rubino et al. |
| 2004/0198762 | A1 | 10/2004 | Naicker et al. |
| 2005/0033046 | A1 | 2/2005 | Chew et al. |
| 2005/0234086 | A1 | 10/2005 | Gu et al. |
| 2005/0234234 | A1 | 10/2005 | Gu et al. |
| 2005/0239178 | A1 | 10/2005 | Ruppen et al. |

FOREIGN PATENT DOCUMENTS

RU    2 233 285 C1    7/2004

OTHER PUBLICATIONS

Moenius, et al., C-14 Labelling of NVP RAD001—A New Rapamycin Derivative, J. Labelled Cpd. Radiopharm., 1999, 42:29-41.

Moenius, et al., Tritium Labelling of RAD001—A New Rapamycin Derivative, J. Labelled Cpd. Radiopharm., 2000, 43:113-120.

Curran, et al. Intramolecular Hydrogen Transfer Reactions of o-(Bromophenyl)dialkylsilyl Ethers. Preparation of Rapamycin-$d_1$, Tetrahedron Letters, 1992, 33(17):2295-2298.

Paiva et al, Incorporation of Acetate, Propionate, and Methionine into Rapamycin by *Streptomyces hygroscopicus*, Journal of Natural Products, vol. 54, No. 1, pp. 167-177, (Jan.-Feb. 1991).

*Primary Examiner*—Bruck Kifle
(74) *Attorney, Agent, or Firm*—David A. Rubin; Howson & Howson LLP

(57) ABSTRACT

41-methoxy-labeled rapamycin 42-ester with 3-hydroxy-2-(hydroxymethyl)-2-methylpropionic acid (CCI-779) compounds are provided, along with methods for the synthesis and use thereof.

25 Claims, No Drawings

41-METHOXY ISOTOPE LABELED RAPAMYCIN 42-ESTER

CROSS-REFERENCE TO RELATED APPLICATIONS

This application claims the benefit under 35 USC 119(e) of U.S. Provisional Patent Application No. 60/733,563, filed Nov. 4, 2005.

BACKGROUND OF THE INVENTION

This invention relates to isotope-labeled compounds of rapamycin 42-ester with 3-hydroxy-2-(hydroxymethyl)-2-methylpropionic acid (CCI-779).

CCI-779 is a derivative of rapamycin, which is a macrocyclic triene antibiotic produced naturally by *Streptomyces hygroscopicus*. The preparation and use of CCI-779 is described in U.S. Pat. No. 5,362,718. Regioselective syntheses of CCI-779 are described in U.S. Pat. No. 6,277,983 and US Patent Publication No. 2005/0033046 A1.

Rapamycin has been found useful in an array of applications based on its antitumoral and immunosuppressive effects. Such uses include preventing, inhibiting, or treating transplant rejection, graft vs. host disease, autoimmune diseases including systemic lupus erythematosis, inflammatory diseases including pulmonary and ocular inflammation, adult T cell leukemia/lymphoma, solid tumors, fungal infections, and hyperproliferative vascular disorders, including smooth muscle cell proliferation and intimal thickening following vascular surgery. Rapamycin and rapamycin derivatives, including CCI-779, continue to be studied for treatment of these and other conditions.

Both radio- and stable-isotope-labeled CCI-779 are required for drug absorption, distribution, metabolism and excretion (ADME) studies and as standard for quantitative mass spectrometry (MS) bio-analytical studies. Clinically useful isotope-labeled CCI-779, either stable-isotope-labeled (e.g., deuterium, $^{13}C$) or radioactive-isotope-labeled (e.g., tritium, $^{14}C$), has been made through labeling its 3-hydroxy-2-(hydroxymethyl)-2-methylpropionic acid side chain. However, this ester-linked side chain has been found unsuitable for labeling due to metabolic instability. Similarly, the 7-methoxy moiety in the rapamycin skeleton is unsuitable for labeling (US Patent Publication No. 2004/0198762 A1).

Accordingly, what is needed are CCI-779 compounds isotope-labeled in metabolically resistant sites having increased metabolic stability and processes for their preparation.

SUMMARY OF THE INVENTION

In one aspect, compounds of isotope-labeled rapamycin 42-ester which are isotope labeled in the rapamycin skeleton, i.e., in a metabolically resistant 41-methoxyl position (41-isotope-labeled compounds of rapamycin 42-esters), are provided. In a further aspect, 41-isotope-labeled compounds of a rapamycin 42-ester bearing carbon isotopes are provided. In one embodiment, the compound is 41-[$^{13}C$]methoxyl CCI-779 (shown below). In another embodiment, the compound is 41-[$^{14}C$]methoxyl CCI-779 (shown below). In a further aspect, 41-isotope-labeled compounds of a rapamycin 42-ester bearing hydrogen isotopes are provided. In one embodiment, the compound is 41-[$^2H_3$]methoxyl CCI-779 (shown below). In another embodiment, the compound is [$^3H_3$]methoxyl CCI-779 (shown below).

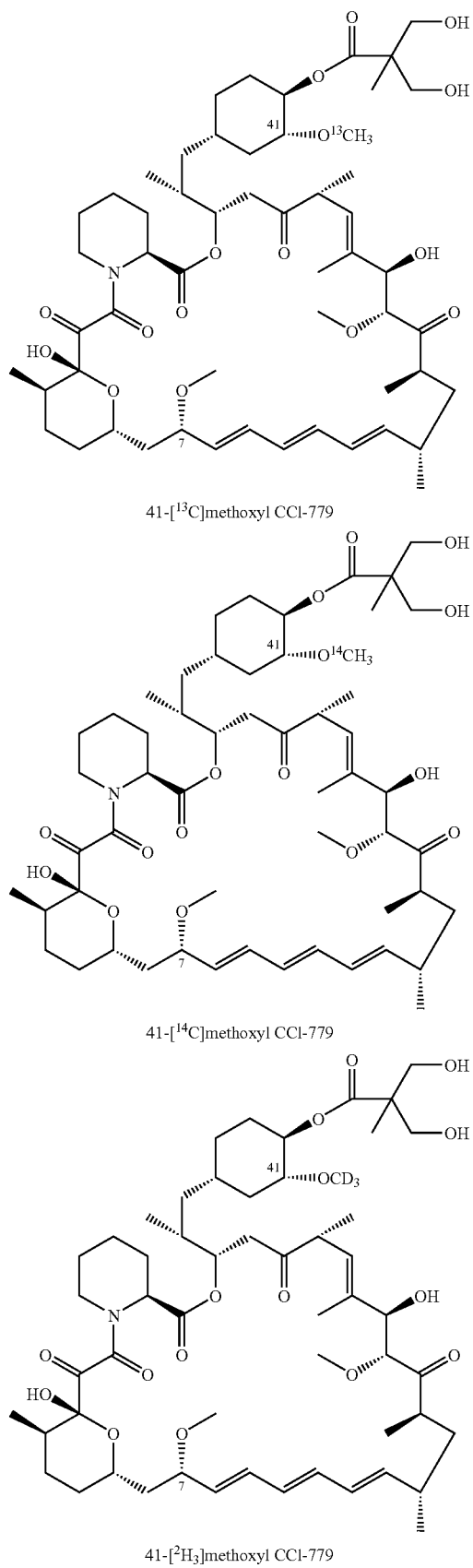

41-[$^{13}C$]methoxyl CCI-779

41-[$^{14}C$]methoxyl CCI-779

41-[$^2H_3$]methoxyl CCI-779

-continued

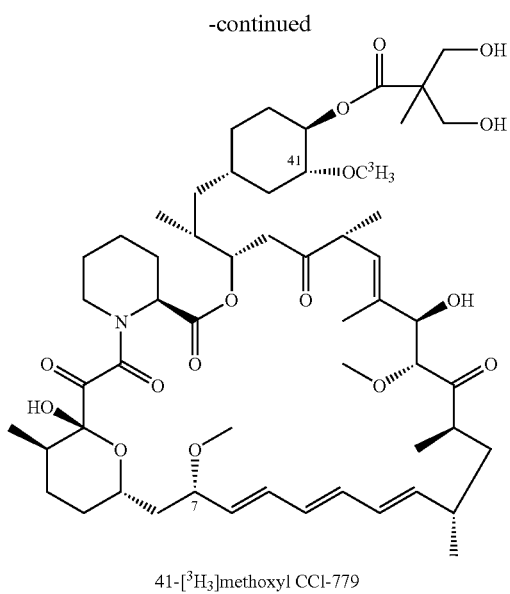

41-[³H₃]methoxyl CCI-779

In another aspect, the processes for the preparation of compounds of the invention from 41-desmethylrapamycin are provided.

In still another aspect, the use of the above compounds in pharmaceutical compositions is provided. In one embodiment, the use of compounds of the invention or compositions containing compounds of the invention in determining pharmacokinetic properties of unlabeled parent compound and for evaluation of ADME data is provided. In another embodiment, the use of compounds of the invention or compositions containing compounds of the invention in bio-analytical study is provided. In still other embodiments, the use of the above compounds and compositions containing the above compounds in the treatment or prevention of, or in the preparation of a medicament useful in the treatment or prevention of, diseases and disorders including transplant rejection, graft vs. host disease, autoimmune diseases including systemic lupus erythematosis, inflammatory diseases including pulmonary and ocular inflammation, adult T cell leukemia/lymphoma, solid tumors, fungal infections, and hyperproliferative vascular disorders, is provided.

Other aspects and advantages will be apparent from the following detailed description of the invention.

DETAILED DESCRIPTION OF THE INVENTION

Isotope-labeled compounds of present invention are rapamycin 42-esters labeled at the 41-methoxyl position in the rapamycin skeleton by reaction of an isotope-labeled methanol alkylating agent with a 41-desmethylrapamycin 42-ester intermediate. In one embodiment, the 41-desmethylrapamycin 42-ester intermediate is a 41-desmethylrapamycin 42-ester with 3-hydroxy-2-(hydroxymethyl)-2-methylpropionic acid.

As used herein, the term "metabolically resistant" refers to an isotope-labeled compound that is labeled at a site resistant to degradation in metabolic reaction, i.e., is sustainable toward metabolic reactions such as hydrolysis, hydroxylation, demethylation, oxidation, etc., under physiological conditions. Compared with compounds having isotopes incorporated at the site of metabolism, e.g., in the acid side chain or at the 7-methoxyl position, these "metabolically resistant" compounds can provide more accurate information due to their longer in vivo half-life.

An isotopic label is made of an element or group which has a plurality of stable isotopes of at least one element constituting the element or group, wherein at least one stable isotope of the constituent element is so controlled that it is present in an amount higher than the natural isotopic abundance ratio (although both are same structurally, the content ratio of the stable isotope of the element is so controlled as to be not lower than the natural isotopic abundance ratio).

Labeling in metabolically resistant sites, e.g., the 41-methoxy site in the CCI-779 skeleton, is useful in obtaining compounds having multiple labeling and compounds having improved metabolic stability. Such compounds are more useful for the evaluation of ADME data.

As used herein, the terms "provide", "providing", and variants thereof, mean administering one or more compounds or compositions described herein to a mammal in need thereof.

As used herein, the terms "prevent", "preventing", and variants thereof, mean providing one or more compounds or compositions described herein to a mammal susceptible to one or more diseases or conditions. As used herein, the terms "inhibit", "inhibiting", and variants thereof, mean providing one or more compounds or compositions described herein to a mammal having one or more diseases or conditions so as to stop or reduce the progress thereof. As used herein, the terms "treatment", "treating", and variants thereof, mean providing one or more of the described compounds or compositions to a mammal having one or more diseases or conditions so as to prevent, inhibit, palliate, or eradicate the disease(s) or condition(s), or to reduce the symptoms thereof.

Throughout the specification, the words "comprising," "including," and "having" and variations thereof are intended to be inclusive and mean that there may be additional elements other than the listed elements.

I. Synthesis

The compounds described are prepared according to the following general synthetic scheme:

Scheme 1: Synthesis of 41-methoxy isotpe labld rapamycin 42-esers

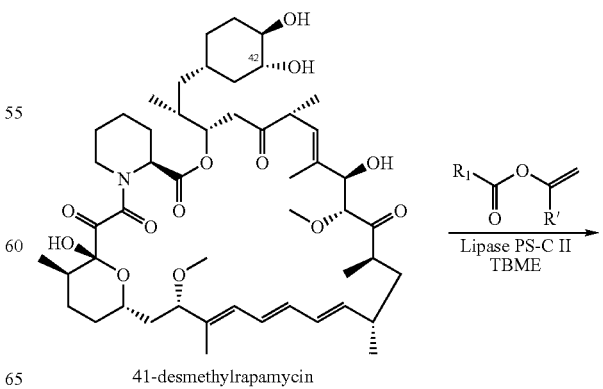

41-desmethylrapamycin

-continued

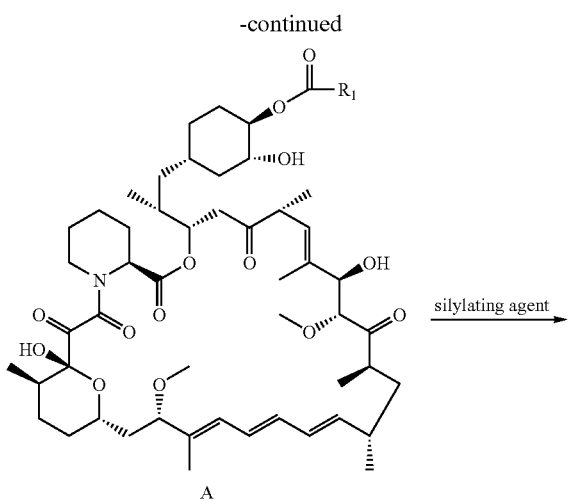

A

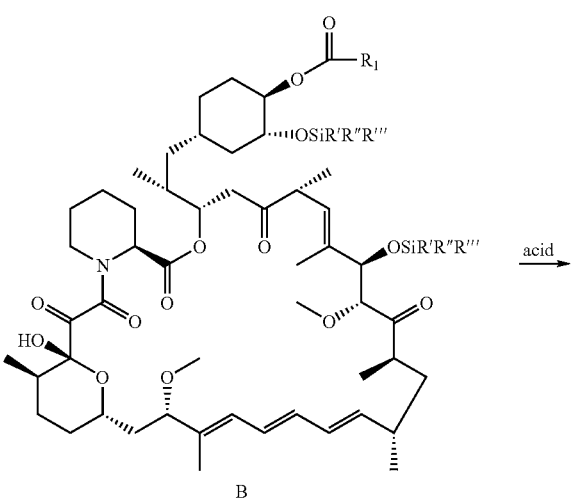

B

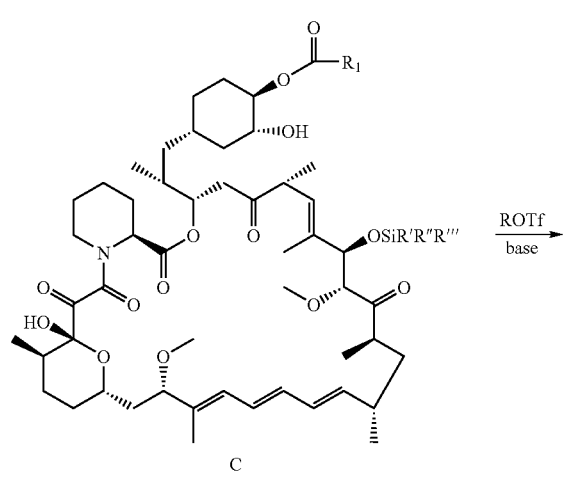

C

-continued

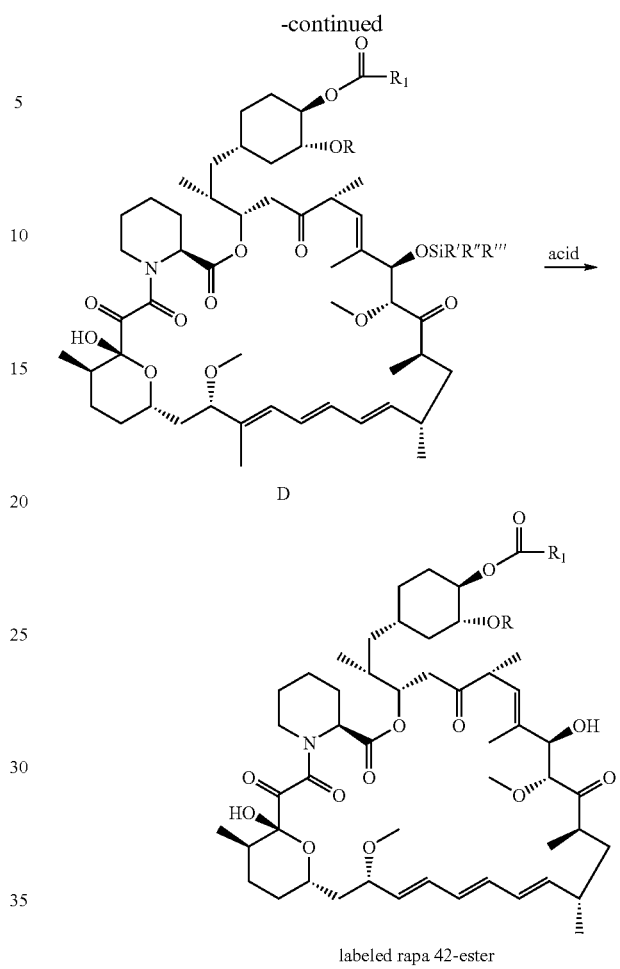

D labeled rapa 42-ester wherein

R is $^{13}CH_3$, $^{14}CH_3$, $C^2H_3$, or $C^3H_3$.

$R_1$ is a linear, cyclic, aromatic, saturated or unsaturated hydrocarbon which optionally contains hydroxyl, boron, nitrogen, halogen and/or thio.

R' is selected from H, Me.

The first step in the synthesis of 41-methoxy isotope-labeled rapamycin 42-ester compounds of the invention is the attachment of an ester side chain onto position 42 of 41-desmethylrapamycin. Unlike rapamycin which contains two secondary hydroxyl groups at position 31 and 42, its preparation of 42-esters can be performed either by non-regioselective chemical reacting rapamycin with various acylating agents or by lipase-catalyzed regiospecific esterification method (US patent application 2005/0234234A1). 41-desmethylrapamycin, on the other hand, is much more complicated, in addition to a secondary hydroxyl group at C-31, it contains two very similar 41,42-bishydroxyl group, this makes the selective 42-esterification much more difficult. The invention provides a lipase-catalyzed process for the introduction of 42-ester side chain into 41-desmethylrapamycin molecule. The remarkable features of this simple process are regiospecificity and excellent yield under mild conditions. In one embodiment, this lipase-based process of the invention is illustrated by the installation of an isopropylidene ketal protected (acetonide protected) 2,2-bis(hydroxymethyl)propionic acid side chain to position 42 of 41-desmethylrapamycin, which is useful for preparation of CCI-779 analogs. However, it will be readily understood that other ester side chains can be readily introduced using the method described above. Examples of such ester side chains can be selected from, including, e.g., alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118, 677); carbamate esters (U.S. Pat. No. 5,118,678); aminoesters (U.S. Pat. No. 5,130,307); acetals (U.S. Pat. No. 5,51,413); aminodiesters (U.S. Pat. No. 5,162,333); alkoxyesters (U.S. Pat. No. 5,233,036); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); U.S. Pat. No. 5,665,772); and PEG esters of rapamycin (U.S. Pat. No. 5,780,462). The preparation of these esters and ethers is described in the patents listed above.

Production of desmethylrapamycins (also known in the art as O-desmethylrapamycins) has been described. See, e.g., U.S. Pat. No. 6,358,969 (29-desmethylrapamycin) and U.S. Pat. No. 6,670,168 (17-desmethylrapamycin), both of which are hereby incorporated by reference. The numbering convention for rapamycin has been changed. Therefore, according to Chemical Abstracts nomenclature, the compounds described above would be at 32- and 8-positions. In one embodiment, 41-desmethylrapamycin may be obtained via biotransformation either by *Streptomyces* sp. ATCC 39471 (Nishida, H. et al, The Journal of Antibiotics, 48(7), 1995, 657-666) or by *Streptomyces rimosus* ATCC 28893 (Kuhnt M., et al, Enzyme and Microbial Technology, 21, 1997, 405-412).

The installation of 42-ester side chain (e.g., isopropylidene ketal protected 42-ester 3-hydroxy-2-(hydroxymethyl)-2-methylpropionic acid) in the first step, as shown in Scheme 1 above, is accomplished via a lipase-catalyzed acylation of 41-desmethylrapamycin with an activated ester, e.g., vinyl esters, isopropenyl esters and anhydrides. In one embodiment, the activated ester derivative is vinyl ester of the 2,2-bis(hydroxymethyl)propionic acid (1). However, other ester side chains are readily selected by one of skill in the art, in one embodiment, the activated ester side chain is selected from among esters of the formula $CH_2=CH-O-COR^1$, where $R^1$ is linear, cyclic, aromatic, saturated, or unsaturated hydrocarbon chain, which optionally contains hydroxyl, boron, nitrogen, halogen and/or thio, in another embodiment, such activated ester side chains are isopropenyl esters having the structure $CH_2=C(CH_3)-O-COR^1$, wherein $R^1$ is defined above.

The acylation reaction may be carried out using a catalytic effective amount of any suitable lipase in a suitable solvent. In one embodiment, the lipase used is a microbial lipase. As used herein, "microbial lipases", i.e., lipases with microbial origin, include enzymes which were originally isolated from a non-eukaryotic source, such as, *Aspergillus niger, Candida antarctica, Candida rugosa, Mucor miehei, Pseudomonas cepacia, Pseudomonas fluorescens, Rhizopus delemar*. However, the enzyme selected for use need not be directly isolated and purified from the original source, but can be prepared synthetically, recombinantly, or through other suitable means. A variety of these enzymes are available from commercial sources. Further, these enzyme preparations can be used as crude, partially purified, purified or immobilized form from different microbial origin under different trade names by various suppliers. In one embodiment, the lipase is lipase PS from *Pseudomonas cepacia*. In another embodiment, the lipase is an immobilized lipase PS from *Pseudomonas cepacia*. In a further embodiment, the lipase is lipase PS-C "Amano" II™ (Amano Enzymes, Inc.). In yet another embodiment, the lipase is lipase PS-D "Amano" I™ (Amano Enzymes, Inc.).

The reaction is typically carried out in an organic solvent. Suitable solvents include, but are not limited to, toluene, tert-butyl methyl ether (TBME), ethyl ether, THF (tetrahydrofuran), MeCN, $CH_2Cl_2$, $CHCl_3$, $^iPr_2O$, hexane, dioxane, or mixtures including these solvents. In one embodiment, TBME (tert-butyl methyl ether) is used. It will be appreciated by those skilled in the art that the solvent is used in an amount which can effectively dissolve all or part of starting 41-desmethylrapamycin at the beginning and allows the reaction to proceed at a reasonable rate. For example, a solvent, such as TBME, can be used in an amount of at least 4 wt volume (i.e., a volume that is in an excess of 4 times (4×) the amount of 41-desmethylrapamycin to about 10 wt volume), with about 5 to 8 wt volumes being preferred.

TBME (tert-butyl methyl ether) may contain residual water (e.g., about 0.05%) which could decompose the rapamycin compound. In order to minimize this side-reaction, a low amount of moisture is maintained in the reaction system. In one desirable embodiment, anhydrous TBME is used with a standard commercial preparation of the lipase catalyst. In another embodiment, moisture can be controlled through adjusting the amount of water present in the lipase solution by adding a drying agent. In yet another embodiment, a molecular sieve can be used to control the moisture. Since a molecular sieve will slow the reaction down, more enzyme may be added to compensate, or a longer reaction time can be used. In one embodiment, a 5 Å molecular sieve is used. However, other sieve sizes including, but not limited to, 4 Å and 3 Å, can be readily utilized. Suitable molecular sieves are available from a variety of commercial sources. In still another embodiment, drying agents such as $MgSO_4$, $Na_2SO_4$, among others, can be used to control the moisture content.

Other lipases, solvents (including solvent mixtures), are known to those of skill in the art and are encompassed herein.

The acylation reaction is conducted at a temperature low enough to reduce the formation of unwanted by-products, but not so low as to require an unreasonably long reaction time. In one embodiment, the acylation is carried out at from about 20 to about 55° C. In other embodiments, the acylation reaction is carried out at about 25 to 50° C., about 35 to 50° C., about 40 to 50° C., or other ranges therein. For example, in one embodiment, the acylation reaction is carried out at about 40 to 45° C.

In one embodiment, the acylation is carried out as follows. 41-desmethylrapamycin, the protected side chain vinyl ester (1) (e.g., isopropylidene ketal protected 2,2-bis(hydroxymethyl)propionic acid vinyl ester), and lipase PS-C "Amano" II are combined in anhydrous TBME. The mixture is heated under nitrogen at 40-45° C. for about 24 hours or until 41-desmethylrapamycin starting material disappears as monitored by TLC or HPLC. After removing enzyme by filtration, 41-desmethyl intermediate A was obtained in nearly quantitative yield.

In the next step, intermediate A is treated with a silylating agent to form a 31,41-bis-O-silyl ether derivative B. In one embodiment, the silating agent has the formula LV-Si R'R"R''', wherein R', R", and R''' are the same or different and are independently selected from an alkyl of 1, 2, 3, 4, 5 or 6 carbon atoms, phenyl and benzyl, and LV is a leaving group. In one embodiment, the LV is a halide (e.g., Cl, Br, or I). Desirably, silylating agents that can be used for this transformation are readily selected from among trialkylsilyl halides, many of which are commercially available, e.g., chloroalkylsilanes, such as chlorotrimethylsilane, chlorotriethylsilane, chlorotripropylsilane or chlorotriisopropylsilane. In one embodiment, the silylating agent is chlorotrimethylsilane. The bulkier the trialkylsilane, the more time is needed to remove it in acid media in the following step to free the 41-hydroxyl group. One of skill in the art will recognize that reduced reaction time generally results in reduced formation of unwanted by-products.

The silylation reaction is carried out in a suitable organic solvent in the presence of a suitable base, which can be readily selected from among those known in the art, e.g., imidazole, 1-methyl imidazole, trialkylamines and N,N-diisopropylethylamine. In one embodiment, imidazole is used as the reaction can be completed in less than 1 hour. A number of organic solvents can be selected for silylation including, e.g., DMF. In one embodiment, ethyl acetate is the solvent. The reaction may be carried out at ambient temperature, e.g., room temperature, or lower, e.g., 0° C., or about 0-5° C. In one embodiment, intermediate A is treated with excess chlorotrimethylsilane in ethyl acetate at 0-5° C. in the presence of imidazole for 120 minutes to form 31,41-bis-O-trimethylsilyl (TMS) ether B.

Following silylation, without separation and purification, crude B in EtOAc solution is treated with a dilute organic or inorganic acid to selectively remove the less hindered 41-O-silyl group, while retaining the silyl group at the more hindered C-31 position, to provide compound C. In one embodiment, the acid is an inorganic acid such as sulfuric, hydrochloric or phosphoric acid. In a further embodiment, the acid is aqueous sulfuric acid having a concentration less than 2.5 N. In still a further embodiment, about 0.1-1 N, or about 0.5 N aqueous sulfuric acid is used. In one embodiment, the reaction can be completed within 1-3 hours. However, longer reaction times may be used where less reactive silyl protecting groups such as triethylsilyl or tripropylsilyl are employed. In one embodiment, the reaction is carried out at a temperature of about 25° C. or below, from about +10° C. to −5° C., or from about 0° C. to 5° C. In one embodiment, when silylation with chlorotrimethylsilane/imidazole is completed as confirmed by TLC or HPLC, 0.5 N aqueous $H_2SO_4$ is added to the reaction mixture, the reaction mixture is stirred for about 2 hours or monitored by TLC while maintaining the temperature at 0-5° C. Regular workup and purification via silica gel chromatography or recrystallization provides compound C. These and other purification means are known to those of skill in the art and are contemplated by the invention.

An important feature is that various isotope atoms are introduced from a common intermediate at a relatively late stage of synthesis. This strategy offers great flexibility for the synthesis of a variety of 41-methoxylabeled rapamycin 42-esters. The late stage option is also desirable, particularly for radioactive isotope labels, because it minimizes handling of radioactive materials and waste disposal and thus is beneficial for personnel and environmental safety.

Compound C is methylated at the C-41 position in the rapamycin skeleton with an isotope-labeled methanol equivalent (also referred to herein as a methanol alkylating agent or a methylating agent) or comprising one leaving group (LG). Examples of leaving groups include, but are not limited to, sulfonates such as methanesulfonate (mesylate, MsO), p-toluenesulfonate (tosylate, TsO), fluoromethanesulfonate, difluoromethanesulfonate, trifluoromethanesulfonate (triflate, TfO), and halogens (e.g. I, Br, Cl). In one embodiment, the leaving group is triflate. Thus, in one embodiment, the methylating agent is Methyl-$^{13}C$ trifluoromethanesulfonate ($^{13}CH_3OTf$). In another embodiment, the methylating agent is Methyl-$^{14}C$ trifluoromethanesulfonate ($^{14}CH_3OTf$). In yet another embodiment, the methylating agent is methyl-$d_3$ trifluoromethanesulfonate ($CD_3OTf$), where d is understood to represent deuterium ($^2H$). In still another embodiment, the methylating agent is methyl-$t_3$ trifluoromethanesulfonate ($CT_3OTf$), where t is understood to represent tritium ($^3H$).

A number of hindered, non-nucleophilic bases can be used for such methylation. Examples of such bases include, but not limited to, 2,6-lutidine, 2,6-di-tert-butylpyridine, 2,6-di-tert-butyl-4-methylpyridine, N,N-dimethylaminopyridine, diisopropylethylamine. In one embodiment, the base is 2,6-di-tert-butyl-4-methylpyridine. In one embodiment, the solvent is toluene, benzene, 1,2-dichloroethane, methylene chloride, or chloroform. However, other suitable solvents may be readily selected by those of skill in the art. In a further embodiment, compound C is treated with an excess amount of labeled methyl triflate in methylene chloride at ambient temperature in the presence of 2,6-di-tert-butyl-4-methylpyridine, followed by purification of the product, compound D, by silica gel chromatography. Modifications in the reaction temperatures and times may be adjusted by one of ordinary skill in the art based on the leaving group utilized and other reaction conditions.

Removal of isopropylidene ketal and 31-silyl protecting groups in compound D to furnish 41-labeled rapamycin ester (e.g., 41-labeled CCI-779) is accomplished by using organic or inorganic acid. In one embodiment, the acid is an inorganic acid such as sulfuric, hydrochloric or phosphoric acid. In a further embodiment, the acid is aqueous sulfuric acid having a concentration less than 4 N. In a further embodiment, about 1-3 N or about 2N aqueous sulfuric acid is used. The reaction is carried out in a water-miscible solvent. In one embodiment, the solvent is acetone. In another embodiment, the solvent is tetrahydrofuran (THF). In one embodiment, the reaction is carried out at a temperature of about 25° C. or below, from about −5° C. to about 10° C., or from about 0° C. to about 5° C. In one embodiment, compound D is dissolved in THF at 0-5° C. and is treated with 2N aqueous sulfuric acid. The progress of the reaction may be monitored by TLC or HPLC. Isotope-labeled CCI-779 was then isolated and purified by silica gel chromatography. This and other purification means are known to those of skill in the art and are contemplated by the invention.

II. Uses and Kits

Currently, the preferred method for following the fate of a drug in vivo is to administer a radiolabelled form of the compound, typically one that incorporates $^{14}C$ or $^3H$ into the structural core. A radiolabel can easily be detected and quantified, making it particularly well suited for use as a tracer. Radioactivity is the gold standard for tracing and measuring the ADME properties of a drug candidate (Dalvie, D., 2000, "Recent advances in the applications of radioisotope in drug metabolism, toxicology and pharmacokinetics", *Curr. Pharm. Des.*, 6, 1009-1028). Hence, Radioisotope-labeled rapamycin 42-ester (e.g., 41-[$^{14}C$]methoxy-CCI-779, and 41-[$^3H_3$]methoxy-CCI-779) is required for drug absorption, distribution, metabolism and excretion (ADME) studies. LC/MS is used extensively to identify drug metabolites, but it is not used quantitatively unless authentic standards of the metabolites are available (Clarke, N. J., et al, 2001, "Systematic LC/MS metabolite identification in drug discovery", Anal. Chem., 73, 430A-439A) and such standards require the incorporation of stable isotope, typically $^{13}C$ and $^2H$ into the core of the molecule. Hence, stable isotope-labelled rapamycin 42-ester (e.g. 41-[$^{13}C$]methoxy-CCI-779, and 41-[$^2H_3$]methoxy-CCI-779) are useful as internal standard of quantitative mass spectrometry (MS) for bio-analytical studies. Moreover, isotopically altered drugs have shown widely divergent pharmacological effects. Petersen et al, found increased anti-cancer effect with deuterated 5,6-benzylidene-dl-L-ascorbic acid (Zilascorb) (Anticancer Res., 1992, 12, 33), and recently, some deuterated rapamycin as therapeutical agents has been incorporated into medical devices (US2003/0130206). Due to the nature of the isotope-labeled rapamycin 42-ester compounds of this invention, i.e., isotope-labeled in a metabolically resistant 41-methoxyl position, they are particularly useful in studying and/or monitoring the pharmacokinetic properties of the rapamycin 42-ester, including the metabolic fate of CCI-779 in the cell/tissue.

Determination of pharmacokinetic properties using radio-labeled rapamycin 42-ester (e.g., CCI-779) as described herein may be accomplished using standard chemical and biological assays and mathematical modeling techniques known to those of skill in the art. For example, the compounds of the invention can be used in the assays such as those described in the following [J. M. Peralba, et al, Clin. Cancer Res, 9:2887-2892 (2003); B Coiffier et al, Blood, 92(6):1927-1932 (Sep. 15, 1998)].

In one embodiment, the invention provides kits for use in detection of particular metabolites of a selected rapamycin 42-ester comprising the counterpart radiolabeled rapamycin 42-ester compound as described herein. In a further embodiment, kits of the invention may also contain additional components, such as, e.g., a positive control (e.g., radiolabeled CCI-779 or a radiolabel-containing metabolite thereof), a negative control, reagents (e.g., buffer, lysozyme, nuclease), vials, tubes, and instructions for performing the method of the invention.

The isotope-labeled rapamycin 42-ester compounds described herein are also useful in the prevention, inhibition, or treatment of transplant rejection, graft vs. host disease, autoimmune diseases including systemic lupus erythematosis, inflammatory diseases including pulmonary and ocular inflammation, adult T cell leukemia/lymphoma, solid tumors, fungal infections, and hyperproliferative vascular disorders, including smooth muscle cell proliferation and intimal thickening following vascular surgery, and other conditions for which rapamycin and its derivatives, including rapamycin 42-ester (CCI-779), has been described. The isotope-labeled compounds described herein are also useful in preparing medicaments useful in the treatment of these diseases and disorders.

In a further embodiment, pharmaceutically effective amounts of the isotope-labeled rapamycin 42-ester compounds described herein are used in the treatment of a disease selected from renal cancer, soft tissue sarcoma, breast cancer, neuroendocrine tumor of the lung, cervical cancer, uterine cancer, head and neck cancer, glioma, non-small cell lung cancer, prostate cancer, pancreatic cancer, lymphoma, melanoma, small cell lung cancer, ovarian cancer, colon cancer, esophageal cancer, gastric cancer, leukemia, colorectal cancer, and unknown primary cancer. The isotope-labeled rapamycin 42-ester compounds described herein are also useful in preparing medicaments useful in the treatment of these diseases.

III. Compositions

The isotope-labeled compounds prepared as described above are useful in pharmaceutical compositions. Such compositions can be formulated by any suitable method described in the art for rapamycin or derivatives thereof.

Oral formulations containing the active compounds as described herein may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In one embodiment, surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, which contains appropriate solubilizers or emulsifiers as needed.

In one embodiment, oral formulations for isotope-labeled CCI-779 of the invention are described in US Patent Publication No. US 2004/0077677 A1, which is hereby incorporated by reference. Other isotope-labeled rapamycin 42-esters may be used in a similar manner. Such an oral formulation contains a granulation prepared using a wet granulation process.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In one embodiment, injectable formulations for isotope-labeled rapamycin 42-ester are described in US Patent Publication No. US 2004/0167152 A1, which is hereby incorporated by reference.

In another embodiment, a useful injectable formulation provides an isotope-labeled-rapamycin 42-ester cosolvent concentrate containing a parenterally acceptable solvent and an antioxidant as described above and a parenteral formulation containing an isotope-labeled rapamycin 42-ester described herein, a parenterally acceptable cosolvent, an antioxidant, a diluent solvent, and a surfactant. Any given formulation may contain multiple ingredients of each class of component. In one embodiment, a parenterally acceptable solvent can include a non-alcoholic solvent, an alcoholic solvent, or mixtures thereof. Examples of suitable non-alcoholic solvents include, e.g., dimethylacetamide, dimethylsulfoxide or acetonitrile, or mixtures thereof. "An alcoholic solvent" may contain one or more alcohols as the alcoholic solvent component of the formulation. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Furthermore, ethanol and propylene glycol can be combined to produce a less flammable product, but larger amounts of ethanol in the mixture generally result in better chemical stability. In one embodiment, the mixture contains an ethanol concentration of 30 to 100% v/v.

In another embodiment, the stability of an isotope-labeled-rapamycin 42-ester of the invention in parenterally acceptable alcoholic cosolvents is enhanced by addition of an antioxidant to the formulation. Acceptable antioxidants include, but are not limited to, citric acid, d,l-α-tocopherol, BHA, BHT, monothioglycerol, ascorbic acid, propyl gallate, and mixtures thereof. Generally, the parenteral formulations useful in this embodiment of the invention will contain an antioxidant component(s) in a concentration ranging from 0.001% to 1% w/v, or 0.01% to 0.5% w/v, of the cosolvent concentrate, although lower or higher concentrations may be desired. In one embodiment, d,l-α-tocopherol is used at a concentration of 0.01 to 0.1% w/v, or 0.075% w/v, of the cosolvent concentrate.

In other embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations). Other chelating agents include such materials as are capable of binding metal ions in solution, such as ethylene diamine tetra acetic acid (EDTA), its salts, or amino acids such as glycine that are capable of enhancing the stability of a rapamycin 42-ester. In still other embodiments, components with chelating activity are included in the formulations as the sole "antioxidant component". In one embodiment, such metal-binding components, when acting as chelating agents, are used in the lower end of the range of concentrations for the antioxidant component provided herein. Additionally, such chelating agents may be used in combination with other antioxidants as part of the antioxidant component of the invention. For example, an acceptable formulation may contain both citric acid and d,l-α-tocopherol. Optimal concentrations for the selected antioxidant(s) can be readily determined by one of skill in the art, based upon the information provided herein.

Advantageously, in certain embodiments of the parenteral formulations, precipitation of an isotope-labeled rapamycin 42-ester upon dilution with aqueous infusion solutions or blood is prevented through the use of a surfactant contained in the diluent solution. The most important component of the diluent is a parenterally acceptable surfactant. In one embodiment, the surfactant is polysorbate 20 or polysorbate 80. However, one of skill in the art may readily select other suitable surfactants from among salts of bile acids (taurocholate, glycocholate, cholate, deoxycholate, etc.) which are optionally combined with lecithin. Alternatively, ethoxylated vegetable oils, such as a pegylated castor oil [e.g., such as PEG-35 castor oil which is sold, e.g., under the name Cremophor EL, BASF], vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60 Other components of the diluent may include water, ethanol, polyethylene glycol 300, polyethylene 400, polyethylene 600, polyethylene 1000, or blends containing one or more of these polyethylene glycols, propylene glycol and other parenterally acceptable cosolvents or agents to adjust solution osmolarity such as sodium chloride, lactose, mannitol or other parenterally acceptable sugars, polyols and electrolytes. It is expected that the surfactant will comprise 2 to 100% w/v of the diluent solution, 5 to 80% w/v, 10 to 75% w/v, 15 to 60% w/v, or at least 5% w/v, or at least 10% w/v, of the diluent solution.

A useful parenteral formulation can be prepared as a single solution. In another embodiment, a parenteral formulation useful in the invention can be prepared as a cosolvent concentrate containing a isotope-labeled rapamycin 42-ester described herein, an alcoholic solvent, and an antioxidant, which is subsequently combined with a diluent that contains a diluent solvent and suitable surfactant. Prior to use, the cosolvent concentrate is mixed with the diluent. When an isotope-labeled CCI-779 described herein is prepared as a cosolvent concentrate, the concentrate can contain concentrations of an isotope-labeled CCI-779 from 0.05 mg/mL, from 2.5 mg/mL, from 5 mg/mL, from 10 mg/mL, or from 25 mg/mL up to approximately 50 mg/ml. The concentrate can be mixed with the diluent up to approximately 1 part concentrate to 1 part diluent, to give parenteral formulations having concentrations of an isotope-labeled CCI-779 from 1 mg/mL, from 5 mg/mL, from 10 mg/mL, from 20 mg/mL, up to approximately 25 mg/ml. For example, the concentration of an isotope-labeled CCI-779 in the parenteral formulation may be from about 2.5 to 10 mg/mL. Also provided is the use of formulations having lesser concentrations of an isotope-labeled CCI-779 of the invention in the cosolvent concentrate, and formulations in which one part of the concentrate is mixed with greater than 1 part of the diluent, e.g., concentrate:diluent in a ratio of about 1:1.5, 1:2, 1:3, 1:4, 1:5, or 1:9 v/v and so on, to parenteral formulations having a isotope-labeled CCI-779 concentration down to the lowest levels of detection.

In one embodiment, the antioxidant may comprise from about 0.0005 to 0.5% w/v of the formulation, the surfactant may comprise from about 0.5% to about 10% w/v of the formulation, and the alcoholic solvent may comprise from about 10% to about 90% w/v of the formulation.

The parenteral formulations can be used to produce a dosage form that is suitable for administration by either direct injection or by addition to sterile infusion fluids for intravenous infusion.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

Further provided are packaging and kits containing an isotope-labeled CCI-779 as described herein formulated for administration by a suitable delivery method. A variety of suitable containers, including bottles, vials, blister packs, and the like are known to those of skill in the art. Such packaging and kits may further contain other components, including, e.g., instructions for use, syringes, applicators, and the like.

EXAMPLES

The following examples are illustrative of the preparation of isotope-labeled rapamycin 42-ester compounds. It will be readily understood by one of ordinary skill in the art from a reading of this application that these examples do not serve to limit the scope of the invention.

A. Synthesis of 41-[$^{13}$C]methoxyl CCI-779 from 41-desmethylrapamycin

The synthesis described herein for 41-[$^{13}$C]methoxyl CCI-779 may be used to generate 41-[$^{14}$C]methoxyl CCI-779, except that the former was accomplished using $^{13}$CH$_3$OTf and the latter is accomplished using $^{14}$CH$_3$OTf. The synthetic scheme is summarized as follows.

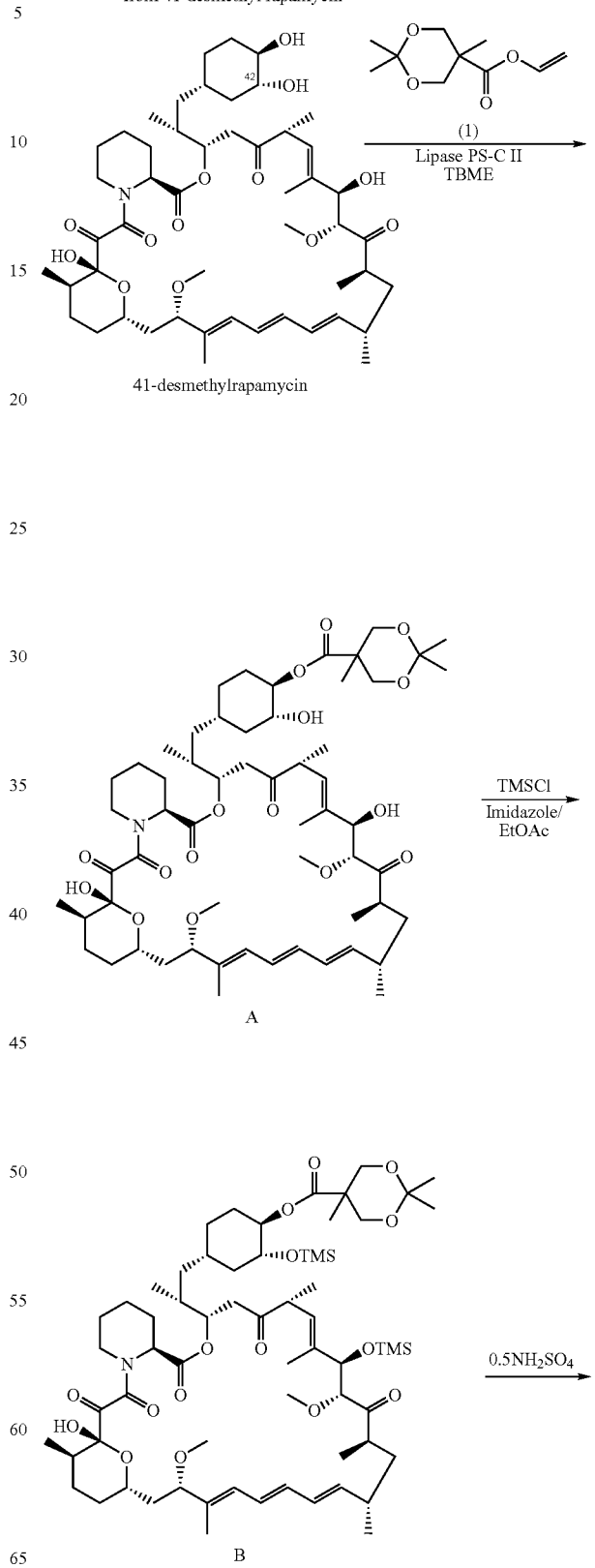

Scheme 2: Synthesis of 41-[$^{13}$C]methoxyl CCl-779 from 41-desmethyl rapamycin

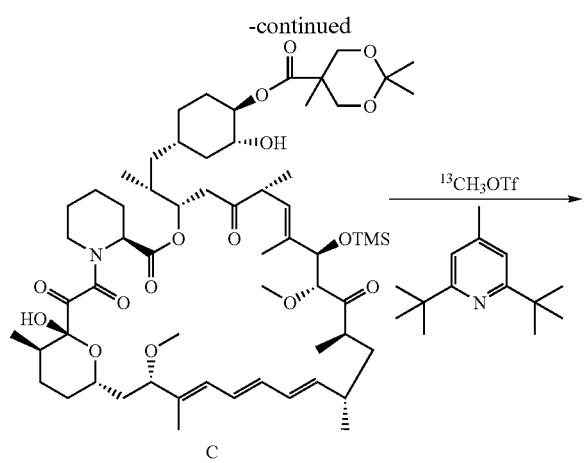

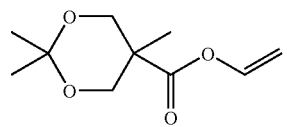

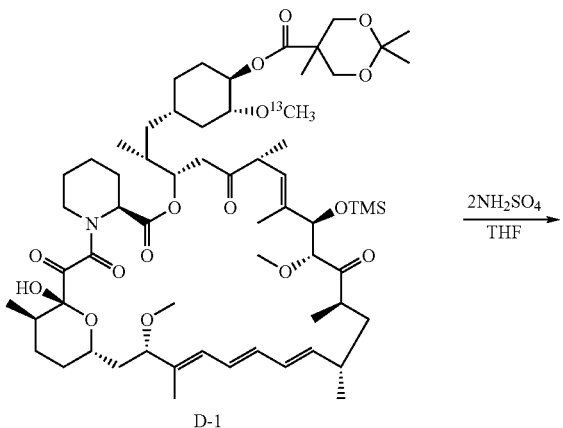

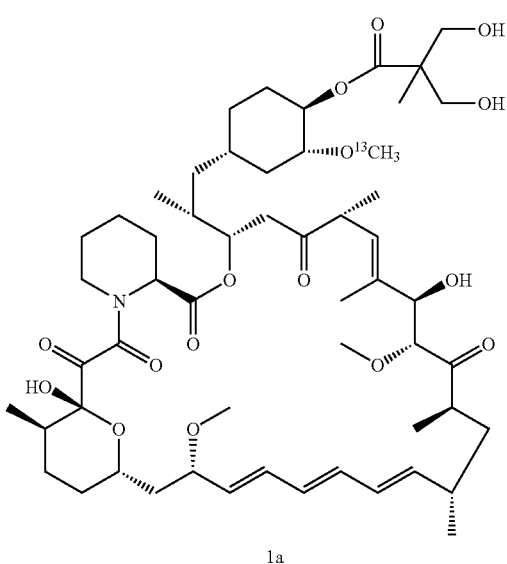

Synthesis of A

A mixture of 41-desmethylrapamycin (770 mg), (1) (500 mg) and lipase PS-C "Amano" II (2.0 g) in anhydrous tert-butyl methyl ether (TBME, 6 mL) was heated under $N_2$ at 40-45° C. for 24 hours. Following the acylation, the enzyme was removed by filtration and washed with TBME. The crude mixture was concentrated to dryness under reduced pressure, crude A was obtained as white form, MS (ESI) m/e 1055 (M⁻).

Synthesis of C

Crude A was dissolved in EtOAc (15 mL) and the mixture was cooled to 0-5° C. with an ice-bath and imidazole (238 mg) was added. To this cold solution chlorotrimethylsilane (324 mg) was added dropwise and the mixture was stirred for 120 minutes. Thin layer chromatography (TLC) indicated all of A was converted to B (31,41-bis-O-trimethylsilyl ether). Diluted aqueous $H_2SO_4$ (2.5 mL, 0.5 N) was then added dropwise to above solution. The mixture was stirred for an additional 3 hours at 0-5° C. and diluted with ethyl acetate (EtOAc) (25 mL)/$H_2O$ (10 mL). The aqueous layer was then separated and extracted with EtOAc. Following extraction, the combined organic layer was washed successively with brine, 5% $NaHCO_3$ and brine, and then dried and concentrated under reduced pressure. Silica gel column purification gave C (650 mg) as white foam, MS (ESI) m/e 1127 (M⁻).

Synthesis of D-1

A solution of C (68 mg) and 2,6-di-tert-butyl-4-methylpyridine (148 mg) in $CH_2Cl_2$ (0.5 mL) was cooled to 0-5° C. To this solution, methyl-$^{13}$C triflate ($^{13}CH_3OTf$) (99 mg) was added dropwise. The mixture was then allowed to warm to room temperature over 1 hour and was stirred for 48 hours. Silica gel column purification of reaction mixture furnished D-1 (42 mg) as white foam [MS (ESI) m/e 1142 (M⁻)].

Synthesis of 1a

A solution of D-1 (20 mg) in tetrahydrofuran (THF) (1 mL) was cooled to 0-5° C. and was treated with aqueous 2N $H_2SO_4$ (0.5 mL). The mixture was then stirred for 24 hours at 0-5° C. The reaction mixture was then diluted with EtOAc (20 mL) and washed successively with brine (5 mL), 5% $NaHCO_3$ (5 mL), and brine (5 mL). The organic layer was dried and concentrated under reduced pressure. The crude product was purified on a silica gel column to give 41-[$^{13}$C] methoxyl CCI-779 (1a) (15 mg) as white foam [MS (ESI) m/e 1075 (M+HCOO⁻)].

B. Synthesis of 41-[²H₃]methoxyl CCI-779 from 41-desmethylrapamycin

The synthesis described herein for 41-[²H₃]methoxyl CCI-779 is the same as that used to generate 41-[³H₃]methoxyl CCI-779, except that the former was accomplished using CD₃OTf and the latter is accomplished using CT₃OTf. The synthetic scheme is summarized as follows.

Scheme 3: Synthesis of 41-[²H₃]methoxyl CCI-779

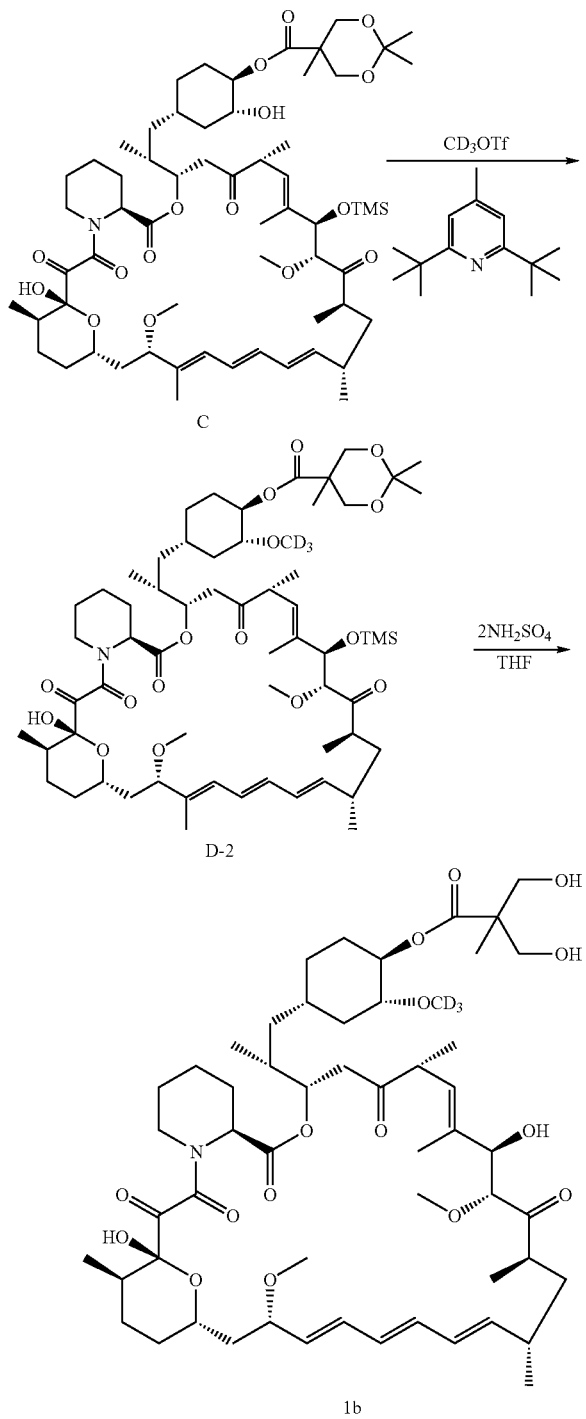

Synthesis of D-2

A solution of C (34 mg) and 2,6-di-tert-butyl-4-methylpyridine (74 mg) in CH₂Cl₂ (0.25 mL) was cooled to 0-5° C. Methyl-d₃ triflate (CD₃OTf) (50 mg) was added dropwise. The mixture was then allowed to warm to room temperature over 1 hour and was stirred for 48 hours. Silica gel column purification of reaction mixture furnished 6 (23 mg) as white foam [MS (ESI) m/e 1145 (M⁻)].

Synthesis of 1b

A solution of D-2 (17 mg) in THF (1 mL) was cooled to 0-5° C. and was treated with aqueous 2N H₂SO₄ (0.5 mL). The mixture was stirred for 24 hours at 0-5° C. The reaction mixture was diluted with EtOAc (20 mL) and washed successively with brine (5 mL), 5% NaHCO₃ (5 mL), and brine (5 mL). The organic layer was then dried and concentrated under reduced pressure. The crude product was purified on a silica gel column to give 41-[²H₃]methyl CCI-779 (1b) (13 mg) as white foam [MS (ESI) m/e 1077 (M+HCOO⁻)].

All documents identified herein are incorporated by reference. One of skill in the art will recognize that minor modifications to the conditions and techniques described in the specific embodiments described herein can be varied without departing from the invention. Such minor modifications and variants are within the scope of the invention described herein and as defined by the following claims.

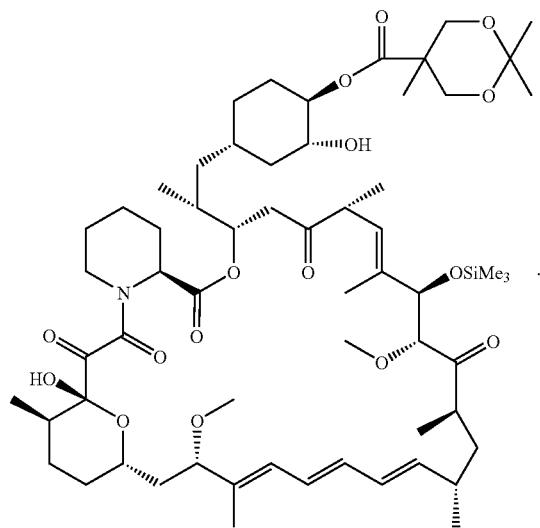

The invention claimed is:

1. A 41-methoxy-isotope-labeled compound of a rapamycin 42-ester, wherein said compound is isotope-labeled on the carbon or hydrogen of the 41-methoxy.

2. The 41-methoxy-isotope-labeled compound according to claim 1, wherein the rapamycin 42-ester is rapamycin 42-ester with 3-hydroxy-2-(hydroxymethyl)-2-methylpropionic acid (CCI-779).

3. The compound according to claim 1, which is 41-[¹³C]methoxyl rapamycin 42-ester with 3-hydroxy-2-(hydroxymethyl)-2-methylpropionic acid (41-[¹³C]methoxyl CCI-779).

4. The compound according to claim 1, which is 41-[¹⁴C]methoxyl rapamycin 42-ester with 3-hydroxy-2-(hydroxymethyl)-2-methylpropionic acid (41-[¹⁴C]methoxyl CCI-779).

5. The compound according to claim 1, which is 41-[²H₃]methoxyl rapamycin 42-ester with 3-hydroxy-2-(hydroxymethyl)-2-methylpropionic acid (41-[²H₃]methoxyl CCI-779).

6. The compound according to claim 1, which is 41-[³H₃]methoxyl rapamycin 42-ester with 3-hydroxy-2-(hydroxymethyl)-2-methylpropionic acid (41-[³H₃]methoxyl CCI-779).

7. A composition comprising a compound according to claim 1 and a pharmaceutically acceptable carrier.

8. A process for preparing a 41-methoxy-labeled rapamycin 42-ester comprising the steps of:
   (a) acylating 41-desmethylrapamycin with an activated ester side chain in the presence of a suitable lipase to provide an 42-ester derivative of 41-desmethylrapamycin;
   (b) treating the compound of step (a) with a silylating agent to form a 31,41-bis-O-silyl ether derivative;
   (c) selectively removing the 41-O-silyl group from the compound of step (b) with an acid;
   (d) treating the compound of step (c) with a labeled methanol alkylating agent; and
   (e) removing the protecting group with an acid.

9. The process according to claim 8, wherein the activated ester derivative in step (a) is isopropylidene ketal protected 2,2-bis(hydroxymethyl)propionic acid vinyl ester.

10. The process according to claim 8, wherein the lipase in step (a) is a microbial lipase.

11. The process according to claim 10, wherein the microbial lipase is an immobilized lipase.

12. The process according to claim 11, wherein the immobilized lipase is lipase PS-C "Amano" II™.

13. The process according to claim 11, wherein the immobilized lipase is lipase PS-D "Amano" I™.

14. The process according to claim 8, wherein the reaction in step (a) is carried out in anhydrous tert-butyl methyl ether.

15. The process according to claim 8, wherein the reaction in step (a) is carried out at 20-55° C.

16. The process according to claim 8 wherein the silylating agent in step (b) is a trialkylsilyl halide.

17. The process according to claim 16, wherein the trialkylsilyl halide is chlorotrimethylsilane.

18. The process according to claim 8, wherein the acid in steps (c) and (e) is sulfuric acid.

19. The process according to claim 8, wherein the isotope-labeled methanol alkylating agent in step (d) is Methyl-$^{13}$C trifluoromethanesulfonate.

20. The process according to claim 8, wherein the isotope-labeled methanol alkylating agent in step (d) is Methyl-$^{14}$C trifluoromethanesulfonate.

21. The process according to claim 8, wherein the isotope-labeled methanol alkylating agent in step (d) is Methyl-$d_3$ trifluoromethanesulfonate.

22. The process according to claim 8, wherein the isotope-labeled methanol alkylating agent (d) is Methyl-$t_3$ trifluoromethanesulfonate.

23. A method for monitoring the pharmacokinetic properties of a rapamycin 42-ester with 3-hydroxy-2-(hydroxymethyl)-2-methylpropionic acid (CCI-779) comprising assaying a sample from a subject to which CCI-779 has been administered using the 41-methoxy isotope-labeled CCI-779 according to claim 1.

24. A method for the treatment of a disease selected from the group consisting of: renal cancer, soft tissue sarcoma, breast cancer, neuroendocrine tumor of the lung, cervical cancer, uterine cancer, head and neck cancer, glioma, non-small cell lung cancer, prostate cancer, pancreatic cancer, lymphoma, melanoma, small cell lung cancer, ovarian cancer, colon cancer, esophageal cancer, gastric cancer, leukemia, and colorectal cancer;

comprising administering to a mammal in need thereof a pharmaceutically effective amount of a compound of claim 1.

25. A compound which is rapamycin 31-O-trimethyl silyl ether, 42-ester with 2,2,5-trimethyl[1,3-dioxane]-5-carboxylic acid having the structure